(12) United States Patent
Pattou et al.

(10) Patent No.: US 8,642,315 B2
(45) Date of Patent: Feb. 4, 2014

(54) PROCESS FOR PRESERVING INSULIN-SECRETING CELLS INTENDED TO BE TRANSPLANTED IN A PATIENT

(75) Inventors: Francois Pattou, Lille (FR); Julie Kerr-Conte, Lille (FR); Cecile Coissac Blondel, Lille (FR); Bruno Lukowiak, Aubigny en Artois (FR); Brigitte Vandewalle, Lille (FR); Antoine Heron, Marlenheim (FR)

(73) Assignees: Maco Pharma, Mouvaux (FR); Centre Hospitalier Regional Universitaire de Lille, Lille Cedex (FR); Universite du Droit et de la Sante de Lille 2, Lille (FR)

( * ) Notice: Subject to any disclaimer, the term of this patent is extended or adjusted under 35 U.S.C. 154(b) by 743 days.

(21) Appl. No.: 12/466,522

(22) Filed: May 15, 2009

(65) Prior Publication Data
US 2009/0286315 A1 Nov. 19, 2009

(30) Foreign Application Priority Data
May 16, 2008 (FR) .................................... 08 02699

(51) Int. Cl.
*C12N 1/00* (2006.01)
*C12N 1/04* (2006.01)
*C12N 5/00* (2006.01)
*C12N 5/071* (2010.01)

(52) U.S. Cl.
USPC ........... 435/243; 435/260; 435/373; 424/93.3

(58) Field of Classification Search
USPC .......................... 435/243, 260, 373; 424/93.3
See application file for complete search history.

(56) References Cited

U.S. PATENT DOCUMENTS

| 6,432,698 | B1 * | 8/2002 | Gaugler et al. | 435/296.1 |
| 2006/0246582 | A1 | 11/2006 | Navran, Jr. | |
| 2007/0122904 | A1 * | 5/2007 | Nordon | 435/325 |

FOREIGN PATENT DOCUMENTS

| EP | 1875802 A2 | 9/2008 |
| WO | 2005120576 A2 | 12/2005 |

OTHER PUBLICATIONS

Shapiro et al "Islet transplantation in seven patients with type 1 diabetes mellitus using a glucocorticoid-free immunosuppressive regimen," N Engl J Med 343:230-238, 2000.*
Ryan et al "Five-year follow-up after clinical islet transplantation," Diabetes 54:2060-2069, 2005.*
International Preliminary Examination Report dated Dec. 10, 2008, for French Application FR 0802699.

* cited by examiner

*Primary Examiner* — Jon P Weber
*Assistant Examiner* — Larry Moore
(74) *Attorney, Agent, or Firm* — Bachman & LaPointe, P.C.

(57) ABSTRACT

Process for preserving insulin secreting cells intended to be transplanted, including the following steps: introducing an initial volume of culture medium and insulin-secreting cells into a culture container, providing a culture medium source, and replacing, at time intervals below 8 hours, the culture medium in the culture container with culture medium from the source so as to renew the culture medium contained in the container.

16 Claims, 5 Drawing Sheets

PROCESS FOR PRESERVING INSULIN-SECRETING CELLS INTENDED TO BE TRANSPLANTED IN A PATIENT

BACKGROUND

The invention relates to a process for preserving insulin-secreting cells intended to be transplanted in a patient.

The invention applies to the field of cell therapy for diabetes, which aims to prepare pancreatic islets or islets of Langerhans from pancreases obtained from brain-dead donors. These islets, which include insulin-secreting beta cells are then reinjected into the portal vein of a receiving patient in order to restore this patient's glycemia regulation without the use of daily recombinant insulin injections.

This cell therapy is therefore a beneficial alternative to pancreas transplant, with an easier surgery and fewer complications.

In practice, the pancreatic islets are isolated by enzymatic and mechanical digestion from a donor pancreas, then purified by density gradient. The islets are then perfused directly into the patient or cultivated for 1 to 3 days before transplantation.

This pre-transplantation culture or preservation step has proven to be beneficial at the metabolic and immunologic levels. Indeed, the time spent cultivating the islets can enable the transplant recipient to be prepared. In addition, this culture step enables the necessary quality controls to be performed on the islets before their perfusion.

However, with the current static preservation processes, between 40 and 60% of islets are lost during the first 24-hour period of culture after isolation.

In addition, the islets are cultured in an open environment in standard containers (flasks or Petri dishes) with numerous handlings, leading to a risk of viral or bacterial contamination of the islets.

Numerous studies have been conducted on the composition of the culture medium in order to improve the preservation of the islets in culture.

For example, document WO 2005/120576 proposes adding 50 M of alpha-tocopherol to a culture medium in order to reduce the damage caused to the pancreatic islets by anoxia. Document US 2007/0196810 proposes adding a polymerized hemoglobin to the culture medium used to isolate the pancreas islets. And, in the document US 2006/0246582, a laminin A chain peptide analog is added to the islet culture medium in order to enable the islet culture density to be increased to up to 300 islets/mL.

These media however remain insufficient for obtaining an acceptable survival rate of the islets in culture.

Regarding the conditioning of the islets, it was envisaged in documents EP-A1-1875802 and US 2005/0032205 to use a flexible pouch permeable to oxygen to cultivate the islets. The survival rate of the islets in these flexible pouches also remains insufficient.

SUMMARY OF THE INVENTION

The invention therefore proposes a process for preserving the insulin-secreting cells, enabling a survival rate of above 60% to be obtained for up to 72 hours, and the functionality of the islets, i.e. their capacity to produce insulin once re-implanted in the recipient, to be maintained. In addition, the process is performed under aseptic conditions reducing the risk of bacterial and viral contamination.

To this end, the invention proposes a process for preserving insulin secreting cells intended to be transplanted, including the following steps:
  introducing an initial volume of culture medium and insulin-secreting cells into a culture container,
  providing a culture medium source,
  replacing, at time intervals below 8 hours, the culture medium in said culture container with culture medium from said source so as to renew the culture medium contained in said container.

BRIEF DESCRIPTION OF THE DRAWINGS

Other objectives and advantages will appear in the following description.

DETAILED DESCRIPTION OF THE PREFERRED EMBODIMENT(S)

The insulin-secreting cells include the pancreatic islets and the other types of cells differentiated into insulin-secreting cells, such as adult stem cells (pancreatic, mesenchymatous, hematopoietic, etc.).

In particular, the insulin-secreting cells are pancreatic islets from a pancreas of a brain-dead donor. They are isolated by enzymatic and mechanical digestion of the pancreas, then purified by density gradient. They are then preserved before being transplanted.

The process of the invention applies to the islets thus isolated contained in preparations with a high level of purity, in particular on the order of 90%, but also to preparations with a lower purity, such as below 50%. Even if the purity of the islet preparations is not satisfactory, the process of the invention enables an islet survival rate of above 80% to be obtained for up to 72 hours.

According to the invention, the process for preserving insulin-secreting cells includes the following steps:
  introducing an initial volume of culture medium and insulin-secreting cells into a culture container,
  providing a culture medium source,
  replacing, at time intervals below 8 hours, the culture medium in said culture container with culture medium from said source so as to renew the culture medium contained in said container.

According to a first aspect, the renewal of medium is periodic, i.e. the replacement of the culture medium contained in the container is performed at predetermined, generally regular, time intervals.

For example, culture medium contained in the container is replaced every 2 hours. In particular, culture medium is first removed from the culture container, then culture medium from the source is introduced into the container. When the container is equipped with distinct inlet and outlet orifices, these removal and introduction steps can be simultaneous.

According to a second aspect, the renewal of medium is continuous: culture medium contained in the container is replaced in an uninterrupted manner by culture medium from the medium source. The time interval in this case is zero.

This periodic or continuous renewal is notably early, i.e. it is performed upon placement of the islets in culture after their isolation. By renewing the medium every two hours, the enzymes released by the exocrine tissue are removed from the culture container, providing the islets with more favorable preservation conditions. In addition, the regular renewal of the culture medium allows for a regular supply of oxygen, which also promotes the preservation of the islets.

Figure 1:
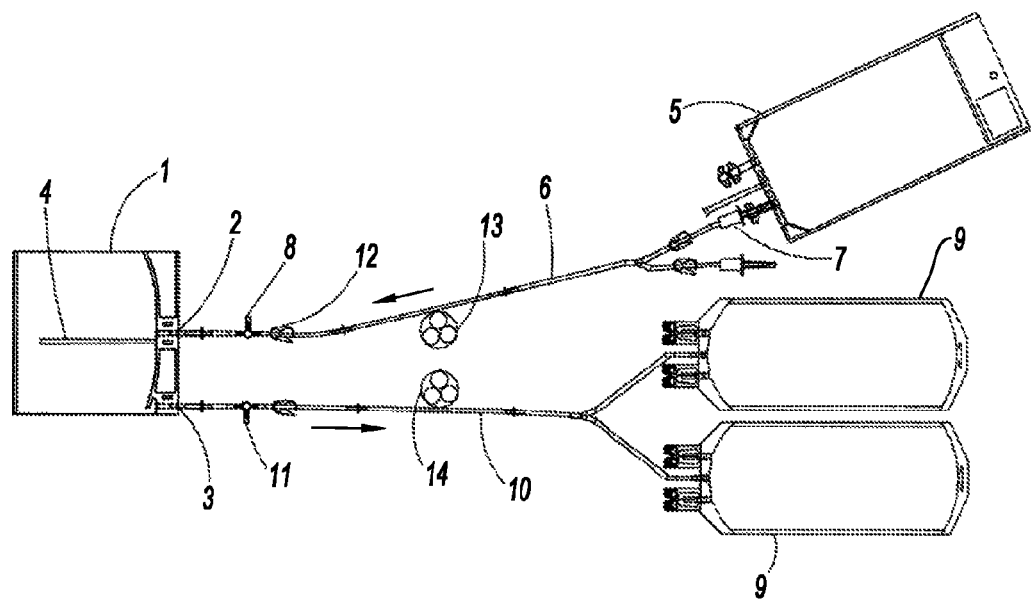
FIG. 1 diagrammatically shows a device for implementing a process of the invention according to which a continuous flow is established in the culture container.

According to FIG. 1, and when the renewal of the medium is performed continuously, the culture container 1 includes at least one inlet orifice 2 and at least one outlet orifice 3, and the replacement of the culture medium is performed by establishing a continuous flow of culture medium coming from the medium source 5, in which said flow is supplied to the culture container 1 by means of the inlet orifice 2 and is removed from said culture container by means of the outlet orifice 3, so as to continuously renew the culture medium contained in said container.

Thus, when the continuous flow is established, a circulation of medium in the culture container is created, so that when the medium is introduced into the culture container, culture medium is simultaneously removed from the culture container.

The continuous renewal of the medium causes a dilution of the enzymes released by the exocrine tissue and thus reduces enzymatic concentrations that are detrimental to the islets.

The concentration of pancreatic islets in the culture medium is between 400 and 40,000 islet equivalents/mL. Advantageously, the concentration of islets is on the order of 500 to 3,000 islet equivalents/mL.

Because the islets can have very different sizes and have a tendency to clump together, it is difficult to define an islet concentration. It is thus preferable to refer to islet equivalents (IE), with an islet equivalent corresponding to a theoretical islet with a diameter of 150 μm.

This relatively high islet concentration with respect to the current preservation processes enables culture containers with an acceptable size for greater ease of handling and an increase in space to be used for preservation.

The culture medium of the insulin-secreting cells such as the pancreatic islets used in the process of the invention includes, in particular, a base medium supplemented with albumin. For example, the base medium is the CMRL-1066 medium. Advantageously, the albumin is natural or recombinant human albumin.

The period for establishing the flow of medium is greater than 24 hours, and in particular between 24 hours and 72 hours. This period is sufficient to enable simultaneously quality controls on an insulin-secreting cell sample and preparation of the recipient for transplantation.

In addition, it is possible that this step of flow-dependent preservation has a positive effect on the quality of the islets.

More specifically, the flow rate of the flow supplied through the inlet orifice of the culture container is between 0.2 and 5 mL/minute, in particular 1.5 mL/minute. This flow rate is advantageously constant throughout the period of establishing the continuous flow.

As the islets must not adhere to the surface of the culture container so as not to lose their functionality, the flow rate must be chosen to be low enough not to drive the islets in the flow of medium out of the container, but high enough to enable sufficient renewal of the culture medium.

Indeed, an islet preparation is not pure at 100%. It comprises a large fraction of exocrine tissue, capable of releasing a large number of molecules including proteases. It is possible that this exocrine tissue is detrimental to the islets and contributes largely to their deterioration. Thus, a renewal of medium limits the presence of proteases and prevents cell death.

In addition, it is recognized, for example in document EP-A1-1875802 that oxygen is beneficial to the survival and functionality of the islets. The continuous renewal of the culture medium also helps to provide oxygen to the islets and promotes their survival.

In particular, the culture container containing the islets is placed at a temperature of between 20° C. and 40° C., and in particular 37° C. To do this, the container, and optionally the other containers and associated tubes, are placed in an incubator.

In association with FIG. 1 and according to a specific aspect of the invention, the culture container 1 includes a biocompatible flexible pouch made of a thermoplastic material. In particular, the material of the pouch in contact with the pancreatic islet suspension prevents adhesion of the islets. For example, the flexible pouch is made of ethylene vinyl acetate.

The concentration and number of islets to be preserved determine the size of the culture container. Flexible pouches having a surface of between 250 and 800 cm$^2$, and in particular 400 cm$^2$, are used. For example, the pouches have a size of 19 cm×20.5 cm in order to obtain a surface of 389 cm$^2$. According to another example, pouches of 18.5 cm×37 cm are used to obtain a surface of 685 cm$^2$.

The culture medium 1 includes at least one inlet orifice 2 for supplying culture medium to the container and an outlet orifice 3 for removing culture medium from the container.

For example, the inlet and outlet orifices 2, 3 of the pouch are formed by tubing portions arranged at the periphery of the pouch, between the two faces of the pouch.

According to FIG. 1, the inlet and outlet orifices 2, 3 are arranged on the same side of the flexible pouch.

In a specific embodiment, to facilitate the circulation of the culture medium in the container, the latter includes at least one deflector 4 arranged on the direct flow path between the inlet orifice 2 and the outlet orifice 3 of the culture container 1.

When the container 1 is in the form of a flexible pouch, the deflector 4 is notably in the form of a weld extending perpendicularly from the side on which the inlet and outlet orifices 2, 3 are arranged, said weld being formed between said orifices.

Thus, the flow is forced to penetrate to the vicinity of the base of the pouch so that all of the culture medium can circulate in the pouch and the islets will be regularly supplied with medium.

When the process is implemented, the inlet orifice 2 of the pouch is in fluidic communication with a container 5 forming, a culture medium source, by means of a first tubing 6.

For example, the container forming a culture medium source, called a source container, includes a flexible pouch, a flask or a bottle containing culture medium. Alternatively, the culture medium source includes a plurality of culture containers 5 in fluidic communication with the culture medium 1.

To enable the connection with the container 5 forming a culture medium source, the end of the first tubing 6 includes a connector 7 such as a perforator.

According to an embodiment, the first tubing 6 is equipped with a device for introducing islets 8. For example, the introduction device is in the form of a three-way connector, in particular a three-way valve. Advantageously, the introduction device 8 is placed as close as possible to the culture container 1 to prevent a loss of islets in the tubing. Even more advantageously, the islet introduction device 8 is in the form of a second inlet orifice of the culture container 1.

The outlet orifice 3 of the culture container 1 is in fluidic communication with a container 9 intended to contain the culture medium removed through the outlet orifice 3, by means of a second tubing 10.

This container 9 intended to contain the culture medium removed through the orifice, called a waste container, is in the form of a flexible pouch, a flask or a bottle.

Alternatively, a plurality of waste containers 9 are in fluidic communication with the culture container 1.

According to an embodiment, the second tubing 10 is equipped with an islet removal device 11. This removal device is identical to or different from the islet introduction device and is in the form of a three-way connector, in particular a three-way valve. Like the introduction device, the removal device is placed as close as possible to the culture container in order to prevent islets from entering the tubing during removal.

In particular, the pancreatic islets are removed from the culture container 1 by suction in a syringe. In an alternative, they flow by gravity into a collection container.

In an alternative not shown, the removal device 11 is arranged on the culture container and forms a second outlet orifice.

According to a specific embodiment, the first and second tubings 6, 10 are equipped with at least one flow regulation device 12 such as a clamp. The tubings are made of a weldable and sterilizable thermoplastic material such as polyvinyl chloride.

To establish a continuous flow of culture medium into said culture container 1, a first peristaltic pump head 13 is associated with the first tubing 6 so as to supply the inlet orifice 2 of the culture container 1 with the flow of medium coming from the source container 5.

Advantageously, a second peristaltic pump head 14 is also associated with the second tubing 10 so as to remove the culture medium flow from the container 1 through the outlet orifice 3.

According to a specific embodiment not shown, a peristaltic pump with two pump heads is used.

When the flow into the culture container 1 is established with the assistance of this first and second peristaltic pump head 13, 14 having an identical rotation speed, the volume of culture medium in the container is constant.

By contrast, when the rotation speed of the first peristaltic pump head 13 is greater than the rotation speed of the second peristaltic pump head 14, the volume of culture medium in the container increases.

According to a specific aspect of the process, the process for preserving islets includes, after introducing the islets into the culture container 1, a stationary phase in which the flow is arranged to keep the volume of culture medium contained in the container 1 at a constant level.

Prior to the stationary phase, and after the introduction of the islets into the container 1, the flow is arranged to increase the initial volume of culture medium in the culture container 1.

For example, 30 mL of culture medium and 45,000 islet equivalents are introduced into a flexible pouch having a surface of 389 cm$^2$. The first pump head 13 is caused to rotate at a speed of 1 mL/min while the second pump head 14 is stopped. When the volume in the pouch is around 90 mL, the second pump head 14 is caused to rotate at a speed identical to the first pump head in order to maintain a constant volume of medium in the pouch.

The rotation speeds of the two pump heads is chosen in particular so that the amount of culture medium coming continuously from the medium source for 2 hours is equivalent to said amount used in a periodic renewal of the medium every 2 hours. For example, if 15 mL of medium is replaced periodically every 2 hours, the rotation speed is chosen so that 15 mL of medium coming from the source have been introduced into the container by the end of a 2-hour period.

Figure 2:
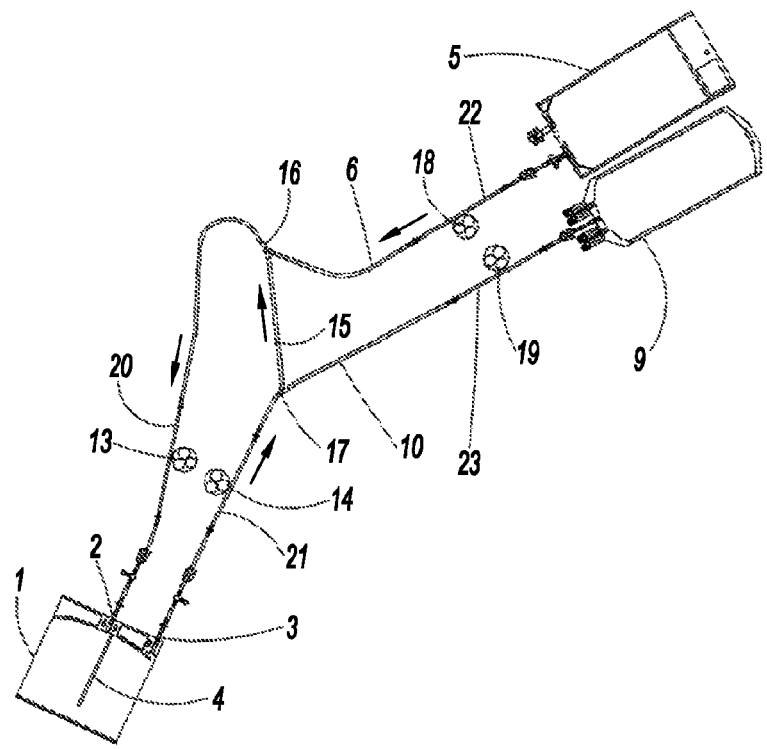
FIG. 2 diagrammatically shows a device for implementing a process of the invention according to which the culture medium that was previously introduced into the culture container is partially recycled.

According to an alternative of the invention shown in FIG. 2, at least some of the flow of culture medium is recycled, i.e. at least some of the flow of culture medium supplying the inlet orifice 2 comes from the flow of culture medium that was previously removed through the outlet orifice 3.

This alternative enables the culture medium to be saved while continuing to renew the oxygen in the culture container.

The process also enables a reduction in the carbon dioxide concentration, which is detrimental to the islets, as well as a reduction in the concentration of enzymes released by the exocrine tissue.

In this alternative and according to FIG. 2, a third tubing 15 is connected between the first and second tubings 6, 10. In particular, the connection is performed with the assistance of a first and a second connection device 16, 17 provided, respectively, on the first and second tubings 6, 10. In particular, the connection device 16, 17 is a three-way connector, such as a T or a Y connector.

According to a specific embodiment, the third tubing 15 is connected to the first tubing 6 upstream of the first pump head 13 and to the second tubing 10 downstream of the second pump head 14. In addition, a third peristaltic pump head 18 is associated with the first tubing, near the source container 5, upstream of the connection 16 with the third tubing 15 and a fourth peristaltic pump head 19 is associated, near the waste container, with the second tubing 10 downstream of the connection 17 with the third tubing 15.

The terms "upstream" and "downstream" refer here to the direction of circulation of the medium in the tubings and the culture containers.

In particular, a second peristaltic pump includes the third and fourth pump heads 18, 19.

Advantageously, the first, second, third and fourth pump heads 13, 14, 18 and 19 belong to the same peristaltic pump head capable of controlling the rotation speed of each of the pump heads.

The tubing portion 20, 21, 22, 23 associated with a pump head 13, 14, 18 and 19 is in particular made of a siliconized material that is more flexible than PVC.

According to FIG. 2, and to ensure the recycling of the culture medium, the third and fourth pump heads 18, 19 have an identical rotation speed, which is slower than the rotation speed of the first and second pump heads.

For example, the rotation speed of the first and second pump heads 13, 14 is 1.5 mL/minute, whereas the rotation speed of the third and fourth pump heads 18, 19 is 0.3 mL/min.

In particular, the flow of culture medium is oxygenated before being supplied to the inlet orifice of the culture medium.

Figure 3:
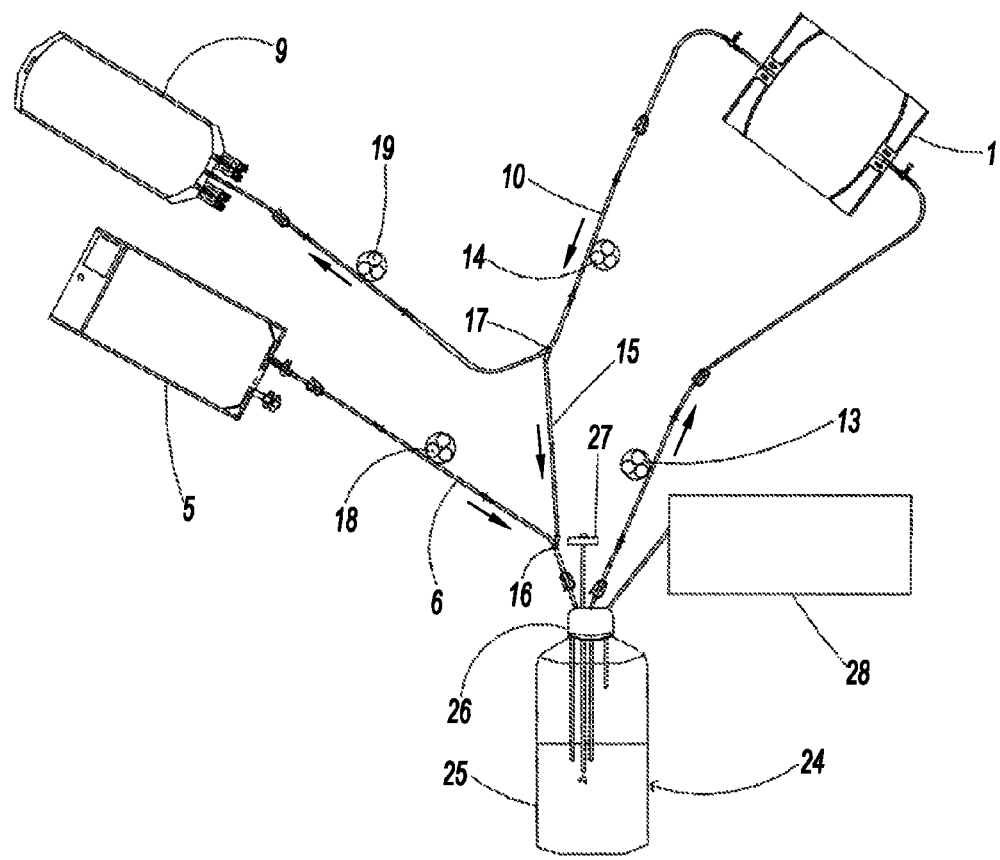
FIG. 3 diagrammatically shows a device for implementing a process of the invention according to which the culture medium is oxygenated prior to its introduction into the culture medium.

To do this, and as shown in FIG. 3, a system 24 for aeration of the culture medium flow is placed on the flow path of the first tubing 6.

According to the alternative shown in FIG. 3, the aeration system is located between the first connection device and the first peristaltic pump head 13.

The aeration system includes an aeration container 25 such as a bottle, an air introduction device 27 such as a tubing portion open to the outside air and equipped with a filter of average porosity of 0.22 μm, and a vacuum pump 28.

The bottle is in particular equipped with a cap 26 provided with two connectors for connection to the first tubing 6, a connector for the air introduction device 27 and a connector for the vacuum pump 28.

According to an alternative not shown, the aeration system includes an oxygenator directly penetrating the source container 5.

According to a specific embodiment, the culture container 1, the tubings 6, 10 connected to said container and optionally the waste container 9 are manufactured in a pre-connected configuration and placed in a sterile packaging. At the time of use, the user then has only to connect the source container 5 and optionally the aeration system 24 in order to obtain a closed culture system meeting the requirements concerning contamination risk reduction.

The device thus obtained enables closed-circuit and safe preservation of the insulin-secreting cells.

EXAMPLES

Example 1

Pancreatic islets were isolated and preserved by regular periodic renewal of the culture medium. Air circulation associated with periodic renewal of the medium (¼ of the volume per hour) was envisaged. The pouches used are on the order of 400 cm$^2$, i.e. similar to those to be used in clinical practice.

The tests were performed on two different islet preparations, the first (Pouch 1) with a mediocre islet purity of 30%, and the second (Pouch 2) with a very high purity of 90%. The partial oxygen pressures (PpO$_2$) are greater in the pouches than in the control dishes. The results are presented in table 1.

TABLE 1

| | Control 1 | Pouch 1 | Control 2 | Pouch 2 |
|---|---|---|---|---|
| Purity | 30% | 30% | 90% | 90% |
| PpO$_2$ (mmHg) | 139 | 151 | 141 | 151 |

The percentage of islet recovery was improved in the pouches; it was on the order of 20% greater than that obtained in the control dishes. It was equivalent in the mediocre preparation where the loss of islets is normally greater than in the purer preparations.

Example 2

In this example, 15,000 islets are placed in a culture dish with 30 mL of medium. Two series of preservation tests were performed, one control without renewal of culture medium (series A), and the other with renewal of the culture medium (series B).

In addition, two culture media were tested: the culture medium M1 including the CMRL medium (In Vitrogen) supplemented with human albumin, and the culture medium M2 including the modified CMRL base medium (Cambrex) supplemented with AB serum and Stem Ease® (Abcys). The renewal was performed by renewing 15 mL of medium every 2 hours for 14 hours (at 2 hours, 4 hours, 6 hours, 8 hours, 10 hours and 14 hours after isolation). The evaluation was performed at 18 hours.

Figure 4:
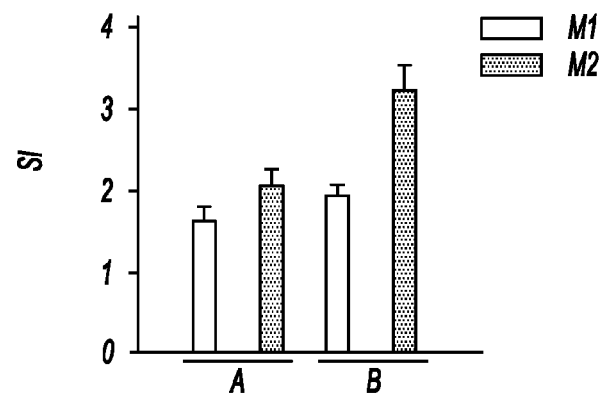
FIGS. 4 to 11 show the evaluation of pancreatic islets preserved according to a process of the invention in the M1 culture medium or the M2 culture medium.
Figure 5:
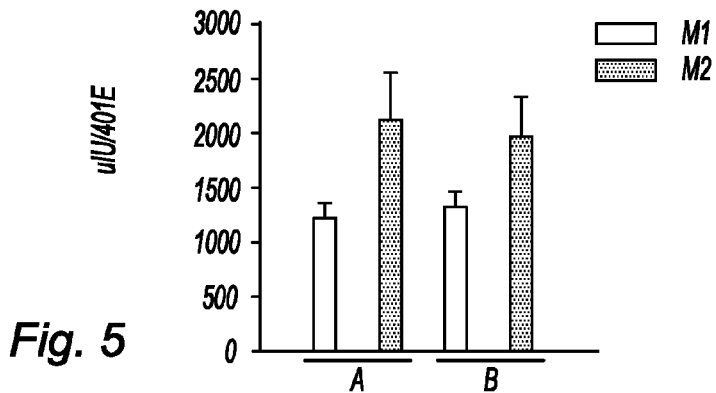
Figure 6:
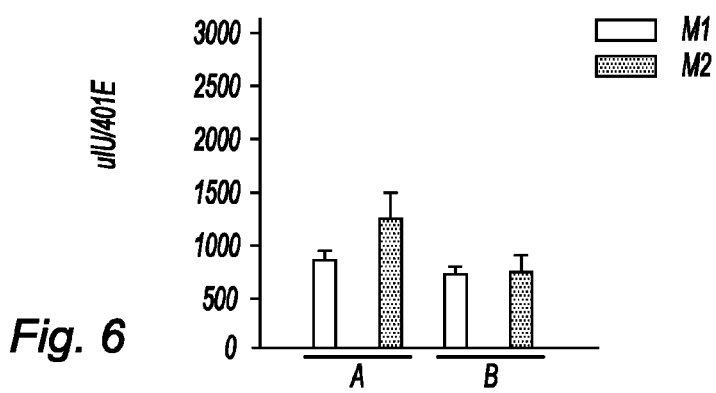
Figure 7:
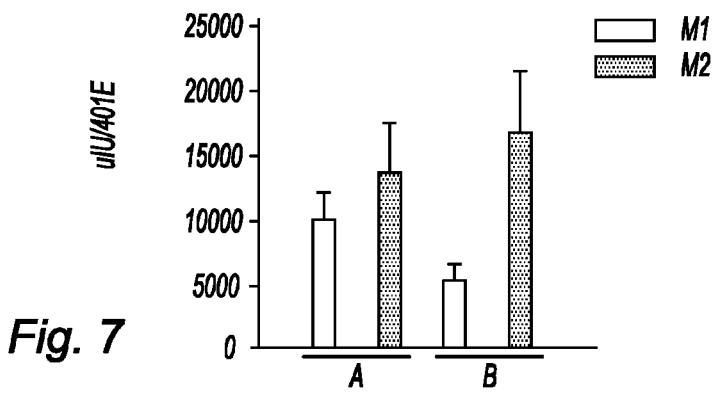
Figure 8:
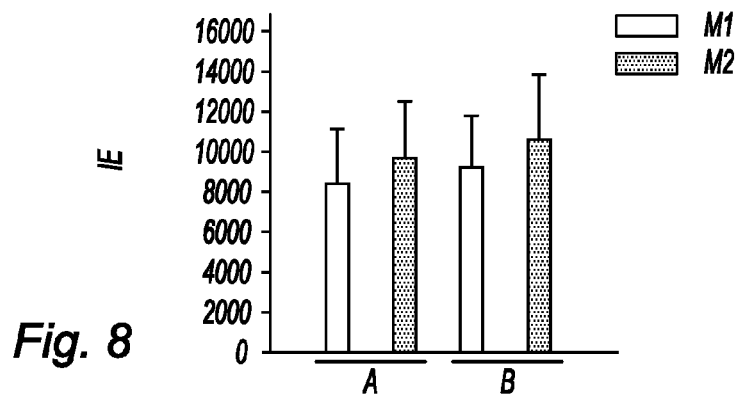
Figure 9:
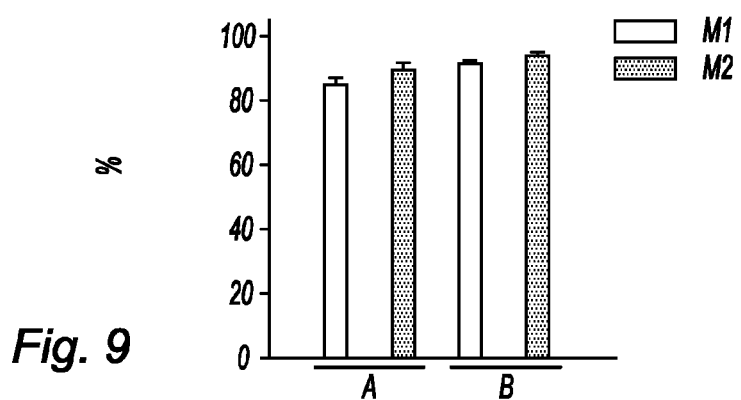
Figure 10:
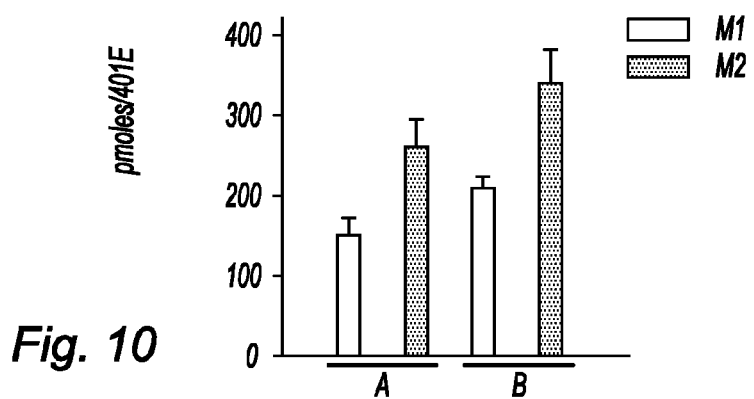
Figure 11:
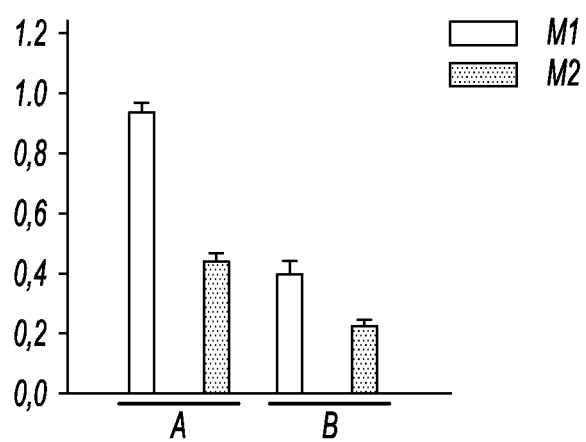

The criteria evaluated were the following:
- the number of islet equivalents (IE) per islet count after staining with dithizone (FIG. 8),
- the physiology of the islets by determining the amount (μIU/40 IE) of insulin (FIG. 7), the insulin secretion level (μIU/40 IE) in response to 20 mM of glucose (FIG. 5) and 2.8 mM of glucose (FIG. 6), and the stimulation index (FIG. 4),
- the cell death per assay (405 nm) by apoptosis (FIG. 11),
- the estimation of the viability of the islets as a percentage (FIG. 9), and
- the determination of the content (pmoles/40 IE) of adenosine triphosphate (ATP) (FIG. 10).

The classic microscopic estimation of viability, purification and cell performance was performed by selective dying of beta cells with dithizone, a specific marker of intracellular insulin, and with Trypan blue, a marker of cell death. The dead beta cells are violet-colored.

The functional activity of the beta cells was evaluated by the intracellular insulin levels and the secretion of insulin in response to glucose stimulation tests.

The intracellular storage and transmission of energy are essentially performed by synthesis and regeneration of adenosine triphosphate (ATP). The ATP contained in the islets was assayed on 3 samples of 40 IE per pancreas, by determining, by luminometry, the reaction between the luciferin and the luciferase using a commercial kit (Perkin Elmer).

Apoptosis is characterized by fragmentation of DNA into mono and oligonucleosomes, which can be detected in cell lysates. The quantification of nucleosomes was performed using the "Cell Death Detection ELISA" kit of Roche Molecular Biochemicals. The detection principle is based on an immunoenzymatic sandwich assay associating monoclonal antibodies directed against DNA and histones. The assay was performed on 3 samples of 160 IE per pancreas.

The insulin content was assayed by a radioimmunological technique using the CT kit of CIS Bio International on the lysates of 3 samples of 40 IE per pancreas. The insulin secretions were estimated during 2 consecutive periods of one hour. The first in the presence of 2.8 mM of glucose and the second at the stimulant concentration of 20 mM of glucose. The stimulation index is defined as the ratio of insulin amounts secreted during these two periods (high over low concentration). The insulin secretions were estimated on 5 samples of 40 IE per pancreas.

It results from the tests (FIGS. 4 to 11) that, when the medium is replaced early and regularly:
- the stimulation index increases from 20 to 30%,
- the islets are not altered and do not excessively secrete insulin at 2.8 mM of glucose,
- the amount of ATP is higher,
- apoptosis is reduced.

The invention claimed is:

1. A process for preserving pancreatic islets intended to be transplanted, including the following steps:
    introducing an initial volume of culture medium and pancreatic islets into a culture container, said pancreatic islets being contained in a preparation comprising exocrine tissue that releases enzymes with concentrations that are detrimental to the pancreatic islets,
    providing a culture medium source having new culture medium,
    replacing, at time intervals below 8 hours, the culture medium in said culture container with said new culture medium from said source so as to renew the culture medium contained in said container, so that the enzymes released by exocrine tissue are removed from the culture container, forming the culture container by a flexible pouch preventing adhesion of the pancreatic islets, providing the culture container with at least one deflector arranged on a direct flow path between an inlet orifice and an outlet orifice of the culture container, and providing said deflector in the form of a weld extending perpendicularly from a side on which said inlet and outlet orifices are arranged, said weld being formed between said inlet and outlet orifices.

2. The process according to claim 1, further comprising introducing a concentration of the pancreatic islets in the culture medium between 400 and 40,000 islet equivalents/mL.

3. The process according to claim 1, wherein said culture medium introducing step comprises introducing a culture medium which includes a base medium supplemented with albumin.

4. The process according to claim 1, wherein said replacing step comprises the culture medium contained in the container every 2 hours so as to periodically renew the culture medium contained in said container.

5. The process according to claim 1, further comprising performing the culture medium replacing step by establishing a continuous flow of culture medium coming from the medium source, in which said flow is supplied to the culture container by means of the at least one inlet orifice and is removed from said culture container by means of the at least one outlet orifice, so as to continuously renew the culture medium contained in said container.

6. The process according to claim 5, further comprising maintaining a stationary phase in which the flow is arranged to keep the volume of culture medium contained in the culture container constant.

7. The process according to claim 6, further comprising prior to the stationary phase, arranging the flow to increase the initial volume of culture medium.

8. The process according to claim 5, further comprising the step of establishing the continuous flow of culture medium comprises establishing the flow in a period greater than 24 hours.

9. The process according to claim 5, further comprising the step of establishing the continuous flow of culture medium comprises establishing the flow in a period between 24 hours and 72 hours.

10. The process according to claim 5, further comprising providing a flow rate of the flow supplying the at least one inlet orifice between 0.2 and 5 mL/minute.

11. The process according to claim 5, further comprising oxygenating the flow of culture medium before being supplied to the at least one inlet orifice.

12. The process according to claim 5, further comprising providing at least some of the flow of culture medium supplying the at least one inlet orifice from the flow of culture medium that has previously been removed through the at least one outlet orifice.

13. The process according to claim 5, further comprising connecting the at least one inlet orifice of the culture container by means of a first tubing to a container forming a culture medium source, in which a first peristaltic pump head is associated with said first tubing so as to supply the at least one inlet orifice with the flow of culture medium coming from said source container.

14. The process according to claim 13, further comprising connecting the at least one outlet orifice of the culture container by means of a second tubing to a container intended to contain the culture medium removed through the at least one outlet orifice, a second peristaltic pump head being associated with the second tubing so as to remove, from the container, the flow of culture medium through the at least one outlet orifice.

15. The process according to claim 14, further comprising connecting a third tubing between the first and second tubings, so that at least some of the flow flowing into the second tubing is reintroduced into the first tubing.

16. The process according to claim 13, further comprising placing a system for aeration of the flow of culture medium on the flow path of the first tubing.

* * * * *